(12) United States Patent
Trutnau

(10) Patent No.: US 9,140,699 B2
(45) Date of Patent: *Sep. 22, 2015

(54) ANALYTICAL MEASURING AND EVALUATION METHOD FOR MOLECULAR INTERACTIONS

(75) Inventor: Hans-Heinrich Trutnau, Eltville (DE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 1019 days.

This patent is subject to a terminal disclaimer.

(21) Appl. No.: 12/891,848

(22) Filed: Sep. 28, 2010

(65) Prior Publication Data

US 2011/0077162 A1 Mar. 31, 2011

Related U.S. Application Data

(63) Continuation of application No. 10/203,169, filed as application No. PCT/EP01/01333 on Feb. 7, 2001, now Pat. No. 7,824,924.

(30) Foreign Application Priority Data

Feb. 7, 2000 (DE) .................................. 100 05 301

(51) Int. Cl.
*G01N 33/543* (2006.01)
*G01N 33/557* (2006.01)

(52) U.S. Cl.
CPC .................................... *G01N 33/557* (2013.01)

(58) Field of Classification Search
CPC ...... G06F 19/70; G06F 19/701; G06F 19/702
See application file for complete search history.

(56) References Cited

U.S. PATENT DOCUMENTS

| | | | |
|---|---|---|---|
| 5,324,633 A | 6/1994 | Fodor et al. | |
| 5,516,635 A | 5/1996 | Ekins et al. | |
| 5,849,535 A | 12/1998 | Cunningham et al. | |
| 5,861,254 A | 1/1999 | Schneider et al. | |
| 6,143,574 A * | 11/2000 | Karlsson et al. | 436/517 |

OTHER PUBLICATIONS

Edwards et al. Analytical Biochemistry, 1997, vol. 246, pp. 1-6.*
Edwards et al. Analytical Biochemistry, 1995, vol. 231, pp. 210-217.*
Zimmermann, B. et al., "PrKX Is a Novel Catalytic Subunit of the cAMP-dependent Protein Kinase Regulated by the Regulatory Subunit Type I." Journal of Biological Chemistry, 1999, pp. 5370-5378, vol. 274, The American Society for Biochemistry and Molecular Biology, USA.
O'Shannessy, D.J., "Determination of kinetic rate and equilibrium binding constants for macromolecular interactions: a critique of the surface plasmon resonance literature." Current Opinion in Biotechnology, 1994, pp. 65-71, vol. 5, Current Biology Ltd., USA.
Canziani, G. et al., "Exploring Biomolecular Recognition Using Optical Biosensors, Methods." 1999, pp. 253-269, vol. 19, Academic Press, Inc., USA.
Rich, R.L. et al., "Advances in surface plasmon resonance biosensor analysis." Current Opinion in Biotechnology, 2000, pp. 54-61, vol. 11, Current Biology Ltd., USA.
Karlsson, R. et al., "Surface Plasmon Resonance Detection and Multispot Sensing for Direct Monitoring of Interactions Involving Low-Molecular-Weight Analytes and for Determination of Low Affinities." Analytical Biochemistry, 1995, pp. 274-280, vol. 228, Academic Press. Inc., USA.
Hoffman, T.L. et al., "A biosensor assay for studying ligand-membrane receptor interactions: Binding of antibodies and HIV-1 Env to chemokine receptors." Proceedings of the National Academy of Sciences of the USA, 2000, pp. 11215-11220, vol. 97, National Academy of Sciences, USA.
Karlsson, R. et al., "Biosensor Analysis of Drug-Target Interactions: Direct and Competitive Binding Assays for Investigation of Interactions between Thrombin and Thrombin Inhibitors." Analytical Biochemistry, 2000, pp. 1-13, vol. 278, Academic Press, Inc., USA.
Myszka, D.G., "Kinetic analysis of macromolecular interactions using surface plasmon resonance biosensors." Current Opinion in Biotechnology, 1997, pp. 50-57, vol. 8, Current Biology Ltd., USA.
O'Shannessy, D.J. et al., "Interpretation of Deviations from Pseudo-First-Order Kinetic Behavior in the Characterization of Ligand Binding by Biosensor Technology." Analytical Biochemistry, 1996, pp. 275-283, vol. 236, Academic Press, Inc., USA.
Morton, T.A. et al., "Interpreting Complex Binding Kinetics from Optical Biosensors: A Comparison of Analysis by Linearization, the Integrated Rate Equation, and Numerical Integration." Analytical Biochemistry, 1995, pp. 176-185, vol. 227, Academic Press, Inc., USA.
Myszka, D. G. et al., "Kinetic analysis of a protein antigen-antibody interaction limited by mass transport on an optical biosensor." Biophysical Chemistry, 1997, pp. 127-137, vol. 64, Elsevier Science B.V.
Sebald, W. et al., "Global and local determinants for the kinetics of interteukin-4/interleukin-4 receptor-chain interaction. A biosensor study employing recombinant interteukin-4-binding protein." European Journal of Biochemistry, 1996, pp. 252-261, vol. 240, The Federation of European Biochemical Societies.
Hensley, P. et al., "Evaluating Energetics of Erythropoietin Ligand Binding to Homodimerized Receptor Extracellular Domains." Methods in Enzymology, 2000, pp. 177-207, vol. 323, Academic Press. Inc., USA.

(Continued)

*Primary Examiner* — Michael Borin
(74) *Attorney, Agent, or Firm* — Sutherland Asbill & Brennan LLP

(57) ABSTRACT

The invention relates to an analytical measuring and evaluation method for determining the interaction parameters between an analyte and a ligand, preferably in a biosensor. According to the inventive method, the concentration of the analyte is gradually changed at defined intervals ti and the initial association or dissociation rates or association and dissociation rate constants are determined. The invention further relates to a device for carrying out the inventive method.

15 Claims, 1 Drawing Sheet

(56) References Cited

OTHER PUBLICATIONS

Myszka, D. G., "Kinetic, Equilibrium, and Thermodynamic Analysis of Macromolecular Interactions with BIACORE." Methods in Enzymology, 2000, pp. 325-340, vol. 323, Academic Press, Inc., USA.
Morton, T.A. et al., "Kinetic Analysis of Macromolecular Interactions Using Surface Plasmon Resonance Biosensors." Methods in Enzymology, 1998, pp. 268-294, vol. 295, Academic Press, Inc., USA.
Myszka, D.G. et al., "Analysis of Fibril Elongation Using Surface Plasmon Resonance Biosensors." Methods in Enzymology, 1999, pp. 386-402, vol. 309, Academic Press, Inc., USA.
Hall, Damien R. et al., "Demonstration of an Upper Limit to the Range of Association Rate Constants Amenable to Study by Biosensor Technology Based on Surface Plasmon Resonance." Analytical Biochemistry, 1996, pp. 175-184, vol. 235, Academic Press, Inc.
Gotoh, M. et al., "A New Approach to Determine the Effect or Mismatches on Kinetic Parameters in DNA Hybridization Using an Optical Biosensor." DNA Research, 1995, pp. 265-293, vol. 2. Kazusa DNA Research Institute.
Doyle, M. et al., "Molecular interaction analysis in ligand design using kinetic and thermodynamic methods." Journal of Molecular Recognition, 1996, pp. 65-74, vol. 9, John Wiley & Sons, Ltd.
Ward, L.D. et al., "Relative Merits of Optical Biosensors Based on Flow-Cell and Cuvette Designs." Analytical Biochemistry, 2000, pp. 179-193, vol. 285, Academic Press, Inc.
Joss, Lisa et al., "Interpreting Kinetic Rate Constants from Optical Biosensor Data Recorded on a Decaying Surface." Analytical Biochemistry, 1998, pp. 203-210, vol. 261, Academic Press, Inc.
Karlsson, Robert et al., "Experimental design for kinetic analysis of protein-protein interactions with surface plasmon resonance biosensors." Journal of Immunological Methods. 1997, pp. 121-133, vol. 200, Elsevier Science B.V.
Karlsson, Robert et al., "Affinity analysis of non-steady-state date obtained under mass transport limited conditions using BIAcore technology." Journal of Molecular Recognition. 1999, pp. 265-292. vol. 12, John Wiley & Sons, Ltd.
Myszka D.G. et al., "Extending the Range of Rate Constants Available from BIACORE: Interpreting Mass Transport-Influenced Binding Data." Biophysical Journal, 1998. pp. 583-594, vol. 75, The Biophysical Society.
Myszka, D.G., "Improving biosensor analysis. Journal of Molecular Recognition." 1999, pp. 279-284, vol. 12, John Wiley & Sons, ltd.
Myszka, D.G., "Survey of the 1998 optical biosensor literature." Journal of Molecular Recognition, 1999, pp. 390-408, vol. 12, John Wiley & Sons, Ltd.
Myszka, D.G. et al., "CLAMP: a biosensor kinetic data analysis program." TIBS: Computer Corner, 1998, pp. 149-150, vol. 23, Elsevier Science Ltd.
Roden, Lin D. et al., "Global Analysis of a Macromolecular Interaction Measured on BIAcore." Biochemical and Biophysical Research Communications, 1996, pp. 1073-1077, vol. 225, Academic Press. Inc.
Shank-Retzlaff, M.L. et al., "Analyte Gradient-Surface Plasmon Resonance: A One-Step Method for Determining Kinetic Rates and Macromolecular Binding Affinities." Analytical Chemistry, 2000, pp. 4212-4220, vol. 72, American Chemical Society.
Myszka, D.G. et al., Equilibrium analysis of high affinity interactions using BIACORE.: Analytical Biochemistry, 1998, pp. 326-330, vol. 265, Academic Press, Inc.
Schuck, Peter et al., "Determination of binding constants by equilibrium titration with circulating sample in a surface plasmon resonance biosensor." Analytical Biochemistry, 1998, pp. 79-91. vol. 265, Academic Press, Inc.
Edwards, Paul R. et al., "Second-order kinetic analysis of IAsys biosensor data: its use and applicability." Analytical Biochemistry, 1998, pp. 1-12, vol. 263, Academic Press, Inc.
Hall, Damien R. et al., "Theoretical and experimental considerations of the pseudo-first-order approximation in conventional kinetic analysis of IAsys biosensor data." Analytical Biochemistry, 1997, pp. 145-155, vol. 253, Academic Press. Inc.
Edwards, Paul R. et al., "Association rate constants by an optical biosensor using initial rate analysis." Analytical Biochemistry, 1997, pp. 1-6, vol. 246, Academic Press, Inc.
Hall, Damien R., "Use of a resonant mirror biosensor to characterize the interaction of carboxypeptidase A with an elicited monoclonal antibody." Analytical Biochemistry. 1997, pp. 152-160, vol. 244, Academic Press, Inc.
George, Andrew J.T. et al., "Kinetics of biomolecular interactions." Expert Opinion on Therapeutic Patents. 1997, pp. 947-963, vol. 7(9), Ashley Publications Ltd.
Casado et al., "Optical association-saturation procedure for estimating association and dissociation rate parameters in receptor studies." Biochemical Journal, vol. 281, pp. 477-483, 1992.
Nice et al., "Analysis of the interaction between a synthetic peptide of influenza virus hemagglutinin and monoclonal antibodies using an optical biosensor." Molecular Immunology, vol. 33, No. 718, pp. 659-670, 1996.
O'Shannessy, D.J. et al., "Determination of rate and equilibrium binding constants for macromolecular interactions using surface plasmon resonance: use of nonlinear least squares analysis methods." Analytical Biochemistry, vol. 212, pp. 457-468, 1993.
Pargellis et al., "Determination of kinetic rate constants for the binding of inhibitors to HIV-1 protease and for the association and dissociation of active homodimer." Biochemistry, vol. 33, pp. 12527-12534, 1994.

\* cited by examiner

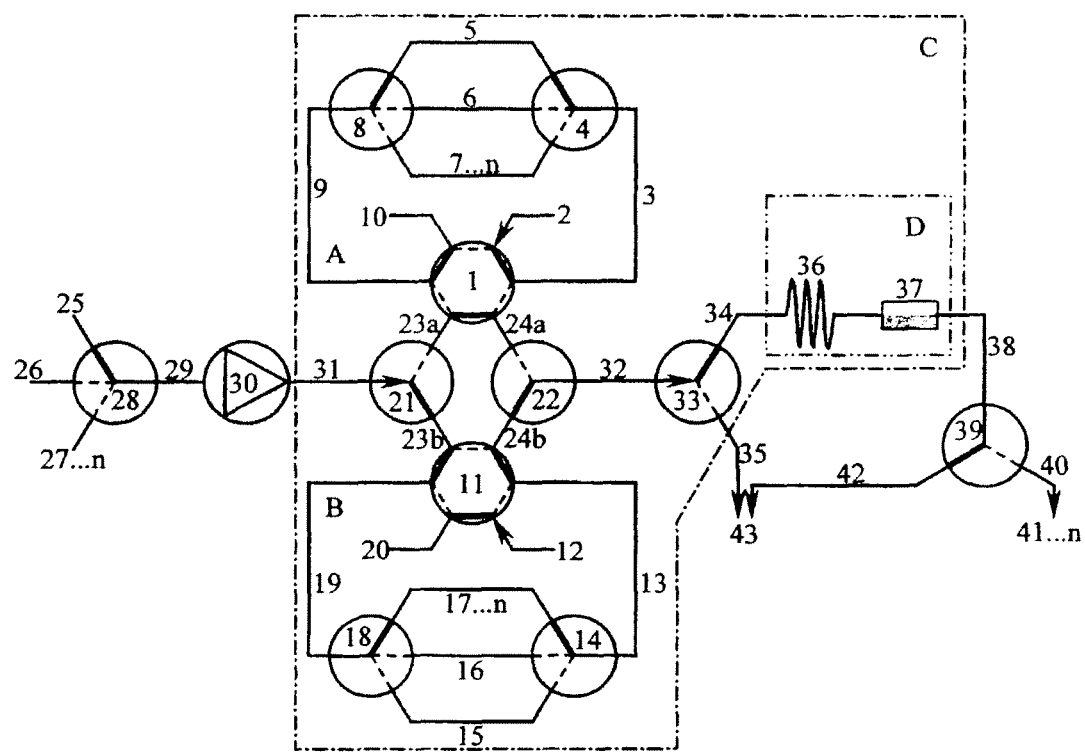

ANALYTICAL MEASURING AND EVALUATION METHOD FOR MOLECULAR INTERACTIONS

CROSS-REFERENCE TO RELATED APPLICATIONS

This application is a continuation of U.S. patent application Ser. No. 10/203,169 filed Nov. 29, 2002, now U.S. Pat. No. 7,824,924, which is a filing under 35 U.S.C. §371 and claims priority to international patent application number PCT/EP2001/001333 filed Feb. 7, 2001, published on Aug. 9, 2001, as WO 2001/057520, which claims priority to German patent application number 10005301.7, filed Feb. 7, 2000.

FIELD OF THE INVENTION

The invention refers to a measurement and evaluation method for determining interaction parameters between an analyte and a ligand, for example including rate constants or binding partner activities. The measured values are acquired, for example, with biosensors in which a (generally immobilized) first binding partner (ligand L) has a second binding partner (analyte A) added to it, and formation of the ligand-analyte complex LA is detected as a function of time.

So-called biosensors for detecting the time courses of the formation of analyte-ligand complexes are known in a wide variety of embodiments, and other apparatuses, for example including array systems, are also usable for detecting such reactions. What are detected are both the time courses of the association of the analyte on the ligand when the analyte concentration is increased by adding an analyte solution of a specific concentration, as well as the dissociation upon addition of a lower-concentration solution or one of zero concentration. In general, the time course of complexation is described using the function $R(t)$ or $R_t$, the concentration of the complex or its change over time being referred to as $c_f(LA)$ or $dc_f(LA)/dt$. To a first approximation, a first-order exponential curve is assumed for the time course of function $R$, with exponent $k_{on}$ upon association and $k_{off}$ upon dissociation of the complex. It has hitherto been usual, for detection of these values, to measure the reaction, e.g. the complexation, partially, or until attainment of an equilibrium value $R_{eq}$ at which association of the analyte+ligand complex is in equilibrium with its dissociation. Dissociation of the complex, and a regeneration and washing phase, then follow. This is a very time-consuming process, especially when multiple measurements with different concentration changes need to be performed successively. A further evaluation of the exponents that have been obtained yields the actual kinetic rate constants of interest, but the method requires a constant analyte concentration.

In existing methods for evaluating the measured values, it is usually assumed that the concentration of the analyte added to the ligand is constant, despite complexation. This is approximated, for example, by having the analyte concentration be many times greater than the ligand concentration, or by continuous exchange in the flowthrough system. In actuality, however, a depletion of the analyte or a concentration change always occurs, for example, in the context of association in the cuvette system, with the result that the equilibrium value $R'_{eq}$ that is actually attained differs from the hypothetical value $R_{eq}$ at a constant analyte concentration. Although analysis of the measured values with a second-order approximation function yields a more accurate value for the coefficient of the exponential function, it is nevertheless complicated and requires additional determination or consideration of a number of experimental boundary conditions.

Initial rates are employed for concentration determination. The initial rates are obtained by placing a compensation line at the beginning of the association curve; its slope underestimates the initial rate, however, since the straight line does not take into account the curvature of the curve. It is also known that when plotting the initial rates on a diagram against the analyte concentration $c(A)$, in a context of multiple measurements with different concentrations each time, in theory a straight line through the origin, with slope $R_{max}*k_{ass}$, is obtained, $R_{max}$ being the maximum possible reaction e.g. of the biosensor to addition of an excess of an analyte. The slope of this straight line is, however, also distorted by the underestimate mentioned above, so that this type of diagram is not employed for determining $k_{ass}$.

The measured values are detected using, inter alia, biosensors on the flowthrough principle or cuvette principle, a very wide variety of measurement methods being known in the existing art. In flowthrough systems, a sensor surface on which the ligand is immobilized is impinged upon, for each analysis, by a constant flow of an analyte solution. The approximation of a preselected constant analyte concentration is applied here. In cuvette systems, a measurement cell is filled with an analyte solution and the reaction with the ligand on a sensor surface is detected. Distortion of the measurement results occurs here in particular, since actual reactions cause the analyte concentration to change. When multiple measurement operations with different concentrations are being performed in succession, normally the cuvette is purged with a buffer solution or otherwise regenerated, and then a solution with a different concentration is introduced.

In the context of multiple titrations, i.e. changes in concentration, the measurement curves have hitherto been recorded until complexation has reached an equilibrium state. Only the equilibrium states are used for the determination of further variables, but not of the kinetics or initial rates. Access to the kinetics is in fact explicitly ruled out with multiple-step titrations of this kind.

For flowthrough systems, so-called sample loops arranged sequentially behind one another, which are filled successively and can be purged out into the measurement chamber, are known. The sample loops each have, however, a volume that is exactly defined in a manner that is laborious in terms of production engineering, and between them an undefined extra volume also called the "dead volume." Undesirable mixing of different solutions can occur in the dead volume. The loops cannot be filled from their outlet side, or partially, or even independently of one another; and they cannot be purged into the measurement chamber independently of one another.

BRIEF DESCRIPTION OF THE INVENTION a) Object

Proceeding from the existing art, it is the object of the invention to describe a method with which measurement times for the detection of measured values during complexation can be shortened, actual conditions during complexation (i.e. change in analyte concentration) are taken into account, and multiple measurements can be performed in succession, e.g. in a cuvette, without laborious rinsing operations; and which makes it possible to ascertain the kinetic constants from the initial rates and, under ideal conditions, also from the curve exponents.

b) Manner of Achieving the Object

Advantageous embodiments of the invention are the subject of the respective dependent claims.

The fundamental idea of the invention is that the change in analyte concentration is taken into account during both association and dissociation of the complex. As a result, the function R assumes an equilibrium value $R'_{eq}$ that differs from the value $R_{eq}$. During association, i.e. addition of a higher-concentration analyte to the ligand, a depletion of the analyte occurs during association, the result being that $R'_{eq}$ is less than the theoretical value $R_{eq}$. At the first moment of the reaction, however, i.e. when the analyte solution is introduced e.g. into the cuvette of a biosensor, the initial rate of function R is independent of whether, later on, an analyte depletion occurs due to binding of the analyte to the ligands, or a constant analyte concentration is assumed. At time t=0, no reaction between analyte and ligand has yet taken place. The fact that the actual reaction profile is taken into account also causes the exponential coefficient to change from to $k_{on}$ to $k_{off}$. In reality, however, the relationship between the individual variables of the exponential function is retained, i.e.:

$$k'_{on} * R'_{eq} = \frac{dR_{ass}(t=0)}{dt} \quad (1)$$

and $$k'_{off} * \Delta R' = \frac{dR_{diss}(t=0)}{dt} \quad (2)$$

where $\Delta R'$ is the difference between the equilibrium value for dissociation and the starting value $R_{st}$ of function R.

This means that, for example, the initial rate can be ascertained from the actual measured values. This is also true if the exponential function proceeds on a first-order basis but with two coefficients $k'_{on(1)}$ and $k'_{on(2)}$, the two corresponding initial rates adding up to a overall rate.

It is possible in the context of the invention for the measured curve of function R to be recorded until the equilibrium value $R'_{eq}$, is reached, in order, e.g. using a mathematical program, to ascertain the exponents $k'_{on}$ or $k'_{off}$ and, from them, the initial association or dissociation rates. Preferably, only a portion of the curve is acquired; for example, acquisition of function R can be discontinued at an earlier point in time so as to ascertain the equilibrium situation from an extrapolation of the partial curve. The exponent k is obtained using a nonlinear approximation, but can also be determined by linear regression of the derivative of function R.

From the initial rates, the respective association and dissociation rate constants $k_{ass}$ and $k_{diss}$ can be ascertained using $$\frac{dR_{ass}(t=0)}{dt} = k_{ass} * R_{max} * c_0(A) \quad (3)$$

for the case of complex association, with a starting analyte concentration $c_0(A)$; and $$\frac{dR_{diss}(t=0)}{dt} = k_{diss} * (-R_{st}) \quad (4)$$

for the case of complex dissociation, the variable $R_{st}$ indicating the starting value of function R during dissociation. The starting concentration $c_0(A)$ is generally defined externally by experiment.

The advantage of the invention is that a measurement can be performed several times in succession, e.g. in a cuvette, with a stepwise modification of the analyte concentration each time; it is not necessary to complete each measurement to the point of reaching the equilibrium value, but instead it can be interrupted earlier and the concentration of the analyte can be raised or lowered. It is also possible to perform measurement series with repeated (and also alternatingly successive) increases and decreases in analyte, in order to acquire association and dissociation curves.

Although the starting rates of multiple i-fold association steps are obtained from the sum of the previous and the new association, the net starting rates of the respective association steps can be ascertained, based on equations (1) and (3) stated above for association, using $$k'_{on,i} * (R'_{eq,ass,i} - R'_{st,ass,i}) = (dR_{ass,i}/dt)_{t=0} \quad (5)$$

and $$(dR_{ass,i}/dt)_{t=0} - (dR_{ass,i-1}/dt)_{t=st,ass,i} = (dR_{ass,i,net}/dt)_{t=0} \quad (6)$$

and can be evaluated using $$(dR_{ass,i,net}/dt)_{t=0}/c_{o,i,net}(A) = -k_{ass} * R_{st,ass,i} + k_{ass} * R_{max} \quad (7)$$

which corresponds to a straight-line equation and can be plotted accordingly.

The quotient of the initial net association rate and net starting analyte concentration, plotted against the starting association signal $R_{st,ass,i}$, yields, when fitted linearly, a straight line having a slope $-k_{ass}$ and an X-axis intercept $R_{max}$. The individual phases of multiple dissociation steps from cuvette systems can be evaluated directly using equations (2) and (4) for dissociation.

So-called fit curves, with which the measurement results obtained can be approximated or (if the measurement is discontinued at an early stage) extrapolated, are calculated using mathematical approximation programs which ascertain a first- or higher-order exponential function, or even double exponential function, that approximates the measurement results with the greatest possible accuracy. A curve of this kind can be automatically calculated during the measurement by the evaluation unit e.g. of a biosensor.

The stepwise modification of the concentration in the measurement chamber can be accomplished at any desired points in time during acquisition of the measurement results. Especially recommended, however, is the half-life point of function R, at which the function, for example in the context of an association, has attained half its final value $R_{eq}$.

If the derivative of function R(t) is plotted on a diagram against function R(t), what is obtained, if the plotted values are approximated e.g. with a linear regression, is a straight line whose Y-axis intercept corresponds exactly to the initial rate, which also, in accordance with equation (1), results from the absolute value of the line slope $(-k'_{on})$ and the X-axis intercept $R'_{eq}$.

To simplify the evaluation, it is assumed that the reactions proceed under ideal conditions, i.e. that, in particular, no analyte depletion occurs. This can be approximated, for example in the case of biosensors with flowthrough systems, by implementing a constant flow rate of solution in the measurement chamber, thereby simplifying the approximation functions because, for example, a first-order exponential function can be assumed for the profile of function R.

As stated by equation (3) above for determining the association rate constant, it is also possible, if the other variables are known, to determine the initial concentration $c_0(A)$ of a solution that has just been introduced into a measurement chamber. For this purpose, for example in a preceding series of experiments, a calibration line can be created in accordance with an initial rate $f(c_0(A))$ with known $c_0(A)$ values from the ascertained initial rates; the unknown $c_0(A)$ value of a sample can then be calculated from the calibration line using the initial rate ascertained from the measured values.

It is also possible, especially when cuvette systems are being used, to obtain the dissociation rate constant from the values obtained from an association operation, and vice versa. The reason for this is that, for example in the case of association, no dissociation is yet occurring in the first moment at which the reaction begins. But because function R assumes an equilibrium value at which association and dissociation are in equilibrium, this value also contains information about $k_{diss}$. Reversing this approach results in an analogous result for dissociation. The corresponding equations are:

$$k_{ass} = \frac{\frac{(dR_{diss}/dt)_{t=0}}{\Delta R_{eq-st\_diss}}}{\left(\frac{c_{eq'\_diss}(A)}{R_{eq'\_diss}}\right)_{c_{eq'\_diss}=0} R_{max}} \quad (8)$$

where $\Delta R_{eq-s\_diss}$ corresponds to the difference between the final value (ideally zero) and the initial values of R for dissociation, $c_{eq'\_diss}(A)$ is the concentration of A after dissociation at equilibrium, and $R_{eq'\_diss}$ is the equilibrium value of R after dissociation, and the limit value for $c_{eq'\_diss}=0$ is used in the denominator; and $$k_{diss} = \frac{\frac{(dR_{ass}/dt)_{t=0}}{c_0(A)}}{\left(\frac{R_{eq'\_ass}}{c_{eq'\_ass}(A)}\right)_{R_{eq'\_ass}=0}} \quad (9)$$

with the corresponding values for association.

The method can also be utilized for evaluation with other affinity biosensors or array systems in solution, and with time-resolved ELISA or RIA techniques or other solid-phase-supported systems that are evident from the existing art.

In a cuvette system, in order to implement a constant flow of solution through the measurement chamber, the concentration of the solution is kept constant by continuously adding and removing a portion of the solution. Present for that purpose, for example, are two hollow needles with solutions, with which fresh solution is continuously circulated in the measurement chamber, or with which a portion of the solution is continuously removed and then re-delivered in order to simulate a flowthrough system with constant concentration.

In this case, as also in ideal flowthrough systems with a constant concentration of solution in the measurement cell, function R is approximated using a first-order exponential function, and the following equation applies:

$$k'_{on,i} = k_{ass} * c_{0,i}(A) + k_{diss} \quad (10)$$

where index i indicates the i-th stepwise change in concentration in a multi-step experiment. With this method, both of the rate constants can be ascertained from the same equation.

For ideal flowthrough systems with a starting analyte concentration that is kept constant during an association phase, it has been shown, as is known, that the starting concentration is exactly equal to the dissociation equilibrium constant $K_D = k_{diss}/k_{ass}$ if, at that concentration, half the immobilized ligand molecules are bound to analyte molecules, i.e. if ½ $R_{max}$ has been attained. It can additionally be demonstrated for such a case, however, that the association phase up to the point of attaining the equilibrium value lasts exactly half as long as the subsequent dissociation phase for returning back to the initial value of zero. At higher starting analyte concentrations, association proceeds more quickly. With this precondition the dissociation curve, if it is overlaid on the previous association curve, intersects said association curve exactly at the Golden Section of the association equilibrium value, corresponding to a value of $0.618 \ldots * R_{eq\_ass}$. In other words, the $K_D$ value can be extrapolated by applying different starting analyte concentrations, and by subsequent regression to the intersection measured value described above. Conversely, a starting analyte concentration that is applied numerically in the $K_D$ value must yield the measured intersection value just described; otherwise the interaction being recorded is not proceeding in ideal fashion. In principle, multi-step kinetics permits an analogous approach.

In general terms, especially for cuvette systems with a variable analyte concentration in the measurement cell during a measurement step, the following equations additionally apply:

$$k'_{on} = k_{ass} * c'_{eqass}(A) + k'_{offmax} \quad (11)$$

with a line slope of $k_{ass}$, in which $c'_{eqass}(A)$ is the equilibrium analyte concentration after association, and $k'_{offmax}$ the maximum value of the coefficient of the exponential function for dissociation; and $$k'_{off} = k_{diss} * (-R_{stdiss})/(R'_{eq} - R_{stdiss}) \quad (12)$$

with a line slope of $k_{diss}$, the index "stdiss" denoting the starting value for dissociation.

c) Exemplary Embodiments of the Biosensor

A biosensor known per se, equipped with a sensor surface on which the ligands are immobilized (i.e. bound), is used to carry out the method. This binding can be accomplished, for example, as is known in the existing art, by way of a chemical binding of the ligands or using a receptor matched to the ligands. A measurement chamber or cuvette that can be impinged upon by a solution of the analyte is configured above the sensor surface. A variety of measurement methods can be used to detect complexation (i.e. binding of the analyte to the ligand) and its change over time, for example detecting the reflectivity of the back side of the sensor, which changes with the degree of complexation c(LA). A hollow needle, which is connected to the measurement chamber and either delivers and/or draws out the solution, serves to introduce the solution into the measurement chamber. The measurement chamber can also be equipped with two separate hollow needles for addition/removal. Impingement with a purging fluid through one of the hollow needles is also possible. An apparatus for mixing the solution is present in order to mix the solution in the measurement chamber, so as to prevent concentration gradients in the solution during the reaction; this can be, for example, a vibratory stirrer. Equipping the biosensor with a preferably electronic control system and with suitable measurement devices, in addition to data acquisition software, is evident from the existing art.

According to the present invention, the biosensor is configured in such a way that the solution in the measurement chamber is repeatedly instantaneously exchangeable, at least partially, with solutions having different analyte concentrations, the liquid volume being kept substantially constant. This means that at least a portion of the solution in the measurement chamber, or the entire solution, is removed, and a new solution having a different concentration is delivered substantially simultaneously. By exchanging at least a portion of the solution with another solution having a desired concentration, the overall concentration in the measurement chamber is modified in defined fashion. The manner of exchanging the liquid can be embodied as desired in the context of the invention, or it can be performed as set forth below. In a flowthrough system, the entire solution in the measurement chamber is exchanged; in a cuvette system, at least a portion thereof. The repeated exchange of the solution makes possible a stepwise change in the concentration in the measurement chamber, so that the method according to the present invention can be carried out.

The advantage of the bio sensor according to the present invention is that, for example in cuvette systems, the volume of the solution is kept substantially constant and thus the number of parameters upon mathematical evaluation of the measurement results is decreased. Instantaneous exchange of the solutions moreover results, especially in flowthrough systems, in sharp transitions between individual association and dissociation phases, which is necessary for determination of the initial rates.

Exchange of at least a portion of the solution in the measurement chamber preferably takes place through one or more hollow needles simultaneously. In particular, the solution is removed with one hollow needle, and a new solution having an arbitrarily selectable concentration is delivered using a different needle.

If the hollow needles are arranged separately from one another on the measurement chamber, e.g. opposite one another, removal and delivery can also be accomplished simultaneously; for complete exchange of the solution in a cuvette system, removal and delivery are accomplished in such a way that the measurement chamber is flushed out in order to prevent undesired residues from remaining behind. The hollow needles can also be arranged coaxially, i.e. one extends inside the other, in which context the inner one either removes or delivers the solution.

For conveying the solutions through the hollow needles into or out of the measurement chambers, pumps are provided with which the quantity of solution being conveyed in each case can be metered. So-called micropumps, which permit metering with the desired accuracy in order to remove well-defined quantities of solution from the measurement chamber or deliver them thereto, are used for this purpose. These pumps can be designed, inter alia, as tubing pumps, syringe pumps, or piezoelectric pumps; actuation is accomplished using actuating motors, electrical drives, etc. and they are also electronically controlled.

Mixing of the solution in the measurement chamber can also be accomplished by the fact that using one or more hollow needles, a portion of the solution is drawn out and is immediately pumped back in, so that the solution is continuously circulated and mixed. Circulation is preferably performed at least 1 µL/min in order to ensure a homogeneous concentration of the solution in the measurement chamber during complexation.

A further advantageous embodiment of the invention consists in the fact that two or more so-called sample loops of arbitrary volume, which can be filled manually and/or automatically by means of a sample dispenser, are present in a specific fashion on the measurement chamber. The sample loops are preferably arranged in parallel between two multiple selector valves, this entire arrangement being switchable into the flow via a switching valve. The sample loops can thus be filled, outside the flow, on the one hand independently of one another because of the selector valves, and on the other hand, completely or only partially, for example in order to conserve analyte solution, from their outflow end via the switching valve. After filling, the solution of the most recently filled sample loop is present at the interface to the flow at the switching valve with no other intermediate volumes, i.e. with no so-called dead volume. This means that the measurement chamber can be impinged upon in flowthrough fashion with multiple different solutions from the individual sample loops via the selector valves successively, mutually independently, and with no dead volume, and with no need for any sample loop to be completely flushed out or for the flow to be directed through it into another loop. A variable and instantaneous, stepwise, sample-economizing concentration change, with practically no mixing, is thereby ensured. In addition, the analyte concentration in the solution in the measurement chamber can be kept constant in each case to a first approximation, in order to prevent depletion. Preferably a solution having a different concentration is present in each sample loop, so that measurements with different concentrations can also be performed in immediate succession, or in order to obtain, by controlled activation of sample loops, an concentration intermediate between the values in the individual sample loops. The number of sample loops is practically unlimited, although in the interest of greater flexibility the aforesaid entire arrangement, including the switching valve between e.g. two two-way selector valves positioned in the flow, can readily be duplicated. The one set of sample loops can thus be processed while the other set is being filled, and can be switched into the flow, with practically no dead volume, even before the last loop of the first set has been completely flushed out.

A possible configuration of the sample feed system in, for example, a flowthrough measurement system is reproduced in FIG. 1, which is described below.

With the exception of pump 30, which can be e.g. an injection pump or peristaltic pump, all the other circles symbolize valves, which can be designed as described here. Valves 1 and 11 are switching valves to which the corresponding inlets or outlets of the valves are connected depending on how the two switching positions are set; in FIG. 1, the existing connections are shown with bold lines and the alternative connections with dashed lines. Valves 4, 8, 14, 18, 28 and, if desired, also 21, 22, 33, and 39 are selector valves with which a central connector, depicted using a standard line width, can be connected to one of an arbitrary number of other connectors. Valves 21, 22, 33, and 39 are shown here, by way of example, as two-way selector valves. All the valve positions can be set manually or automatically, and also in preprogrammed fashion using e.g. an electrical or pressure drive system. All the valves are preferably designed as the kind of rotary valves used in chromatography, e.g. with a low-volume micro design, but can also be designed e.g. as solenoid valves. 36 is an arbitrarily dimensionable temperature-control capillary, and 37 is the interaction detection unit (called simply the "detector"), e.g. of the affinity biosensor type. All the connections shown with a standard solid line comprise capillaries, made for example of TEFZEL™, PE™ PEEK™, or stainless steel, having arbitrary dimensions in terms of inside diameter/outside diameter/length, for example 1 mm/$\frac{1}{16}$"/0.5 m for connection 31. A solution of any kind, selected from reservoirs 25 through 27 or n additional ones, is pumped by means of pump 30 either through valve 33 for purging purposes into waste vessel 43, or through detector 37 and directed via valve 39 into waste vessel 43. Solutions of further interest purged out of detector 37 can be collected via valve 39 in collector 41, retrieved in n fractions in multiple containers, or coupled directly to other technologies, e.g. mass spectrometry. The components contained in C, surrounded with a dot-dash line, can be temperature-controlled together by means of a Peltier element (not shown here).

What is particular to the present invention about this part is the manner of feeding in the sample, which is advantageous for repetitive sample feeding and in particular for multi-step kinetics. Components 1 through 10 are grouped together as sample feed system A, and can be switched either via valve 1 directly into connection 31 or, duplicated any number of times, via valves 21 and 22 into connections 31/32; one duplication of A, grouped together with an analogous sample feed system B, is depicted here. In A, valve 1 is in the loading position for sample loops 5 through 7, which can be filled via sample inlet 2, either manually or automatically by means of a specimen dispenser, with any desired solutions, i.e. also with analyte solutions of respectively decreasing concentration, the displaced solutions being purged into waste vessel 10. Minimal volumes, e.g. for microanalyses or test analyses, can be implemented by partially filling only connection 3. Theoretically unlimited maximum volumes of a solution, e.g. for so-called preparations having particularly large sensor surfaces, can be implemented by filling all the sample loops with the same solution.

After respectively synchronous switching of valves 4 and 8, sample loops 5 and 7 can be filled successively and mutually independently and in each case completely or only partially (to conserve sample), and in each instance "backwards," i.e. from their later outlet end. This ensures that after valve 1 has been switched into the flow position, the solution of the most recent filling is present with no dead volume at connection 24a; and that after the switching of valves 4 and 8—at any point in time, stepwise, and synchronously in each case—the solutions of the other sample loops can be allowed to impinge, with no transition and mutually independently, thereon and on detector 37. This impingement is shown in B, where components 11 through 20 are in the flow position as a minor image of A. By preferably synchronous switching of valves 1, 11, 21, and 22, A and B can be alternatingly switched over into the flow and loading positions, so that A is in flow mode while B is being filled, and vice versa. All the connecting capillaries and loops—3, 9, 13, 19, 23a,b, 24a,b, 29, 31, 32, 34, 35, 38, 40, 42 and 5, 6, 7, 15, 16, 17—can be designed with particularly optimized dimensions depending on their application. Purge buffers or so-called run buffers from the last purging run or analytical run are normally present in 24a and/or 24b. If necessary, these connecting capillaries can also be designed with greater volumes so that, after impingement of the solutions from B or A and simultaneous switchover of the solutions from A or B into the flow position, a washing or dissociation phase can first be performed in detector 37, the duration thereof being determined by the volume of 24a or 24b and the flow rate; this may be of interest depending on the application. The arrangement is moreover open for the positioning of further valves and/or pumps for the purpose of washing or purging any desired portions or for the introduction of further solutions. For example, B and/or further duplicates of B can optionally be positioned, via valve 11, e.g. in connections 3, 5, 6, 7, or 32.

Frequent switching of specific valves (different ones depending on the application) furthermore makes possible a mixing of solutions, if necessary also by installation of a flow divider e.g. in connection 31 instead of or in addition to valve 21, and/or of a so-called micro-mixing chamber e.g. in connection 32 instead of or in addition to valve 22. The overall result of this arrangement is maximum flexibility in terms of solution impingement upon the measurement cell. Mixing of reservoirs 25 through 27 or others can also be achieved by frequent switching of valve 28. For solutions that are temperature-sensitive, all or only some of the components contained in C, for example excluding the components contained in D and surrounded with a dash-dot-dot line, can be separately temperature-controlled, while the components e.g. contained in D can in turn be separately controlled to a working temperature.

LIST OF INDICES ass Association
diss Dissociation
i i-th step
st Starting value of a particular association or dissociation
eq Equilibrium value of a particular association or dissociation
net Net
$k_{on}$ Exponential coefficient for association
$k_{off}$ Exponential coefficient for dissociation It is apparent that many modifications and variations of the invention as hereinabove set forth may be made without departing from the spirit and scope thereof. The specific embodiments described are given by way of example only, and the invention is limited only by the terms of the appended claims.

The invention claimed is:

1. An analytical measurement and evaluation method for determining kinetic constants for molecular interactions between a first binding partner L (ligand) and a second binding partner A (analyte) forming a complex LA, wherein the first binding partner L is immobilized on a sensor surface of a biosensor, the sensor surface is contacted with a solution containing the second binding partner A, and binding of the second binding partner A to the immobilized binding partner L on the sensor surface is detected over time providing measurement values, the method comprising the following steps:
  raising or lowering several times an analyte concentration $c_n(A)$ of the second binding partner A in a stepwise fashion and before an equilibrium interaction state for the respective analyte concentration $c_n(A)$ has been reached, and without any regeneration of the sensor surface between each raising or lowering of the analyte concentration; and
  determining one or more kinetic constants of the interaction from the measurement values.

2. The method of claim 1, wherein the initial association rate or the initial dissociation rate is ascertained using actual measured values of the rate of complexation between the ligand and the analyte, the actual measured values being acquired prior to the rate of complexation reaching equilibrium.

3. The method of claim 2, wherein all initial rates are ascertained under an assumption of ideal conditions that no analyte depletion occurs upon association and that no analyte enrichment occurs upon dissociation.

4. The method of claim 1, wherein an analyte concentration $c_0(A)$ is ascertained at the beginning of the analytical measurement.

5. The method of claim 1, wherein an analytical measurement and evaluation method is practiced in a cuvette system with a measurement chamber, and wherein the analyte concentration of a solution in the measurement chamber is kept constant during each stepwise raising or lowering of the analyte concentration by continuously removing a portion of the solution from the measurement chamber through a first hollow needle and adding a solution having the analyte concentration through a second hollow needle.

6. The method of claim 5, wherein the analyte concentration in the measurement chamber is raised or lowered between the steps i-1 and i, and wherein the respective concentrations $c_0(A)$ of the analyte are determined for each i-th step.

7. The method of claim 1, wherein determination of kinetic constants comprises determining an association constant $k_{ass}$ and a dissociation constant $k_{diss}$ by:

determining an initial net association rate $(dR_{ass,i,net}/dt)_{t=0}$ as a difference between an initial association rate $(dR_{ass,i}/dt)_{t=0}$ at a starting association value $R'_{st,ass,i}$ of i-th step and a final association or dissociation rate of i-1 step, and determining a net starting analyte concentration $C_{0,i,net}(A)$ as a difference between the analyte concentration of i-th step and the analyte concentration of i-1 step, wherein the initial association rate of i-th step and the final association or dissociation rate of the i-1 step are derived from $R_{ass}(t)$, $R_{diss}(t)$ by non-linear approximation or from their time derivatives by non-linear or linear regression;

determining an initial dissociation rate $dR/dt_{0,diss,i}$ at a starting dissociation value $R'_{st,diss,i}$ by non-linear approximation of $R_{diss}(t)$ or by regression of a time derivative of $R_{diss}(t)$;

determining a difference $(R'_{eq,diss,i} - R'_{st,diss,i})$ between an equilibrium dissociation value of i-th step $R'_{eq,diss,i}$ and the starting dissociation value at the i-th step $R'_{st,diss,i}$; and determining a dissociation rate constant $k_{diss}$ from a relationship between $dR/dt_{0,diss,i}$ and $(R'_{eq,diss,i} - R'_{st,diss,i})$, or determining an association rate constant $k_{ass}$ from a relationship between a quotient $(dR_{ass,i,net}/dt)_{t=0}/c_{0,i,net}(A)$ and $R'_{st,ass,i}$.

8. The method of claim 1, wherein the dissociation rate constant $k_{diss}$ is obtained from the initial dissociation rates and the respective equilibrium association values of the function R(t), and wherein the association rate constant $k_{ass}$ is obtained from the initial dissociation rates and the respective equilibrium dissociation values of the function R(t).

9. The method of claim 1, wherein said analyte concentration $c_n(A)$ of the second binding partner A is the same during more than one of said stepwise raising or lowering of the analyte concentration by successive impingements of solutions or sample loops that contain the same analyte concentration.

10. The method of claim 1, wherein said analyte concentration $c_n(A)$ of the second binding partner A is varying over time within one or more of said individual steps by controlled activation of sample loops that contain different analyte concentrations or by mixing of solutions via frequent switching of specific valves that are connected to different solutions.

11. The method of claim 1, wherein the kinetic constants are the association rate constant $k_{ass}$ and the dissociation rate constant $k_{diss}$.

12. The method of claim 1, wherein the kinetic constants are a dissociation equilibrium constant $K_D = k_{diss}/k_{ass}$ and an association equilibrium constant $K_A = 1/K_D$.

13. The method of claim 1, wherein a dissociation equilibrium constant $K_D$ and an association equilibrium constant $K_A = 1/K_D$ are ascertained from a relationship between an analyte concentration $c_n(A)$ and an equilibrium value $R_{eq,i}$ of said steps.

14. The method of claim 1, wherein a maximum possible reaction $R_{max}$ is ascertained from a relationship between the analyte concentration $c_n(A)$ and an equilibrium value $R_{eq,i}$ of said steps or from a relationship between the analyte concentration $c_n(A)$ and an initial rate of said steps.

15. The method of claim 1, wherein said raising or lowering of the analyte concentration of the second binding partner A is started at any time point.

* * * * *